(12) United States Patent
Rosenbloom

(10) Patent No.: US 7,083,813 B2
(45) Date of Patent: Aug. 1, 2006

(54) METHODS FOR THE TREATMENT OF PERIPHERAL NEURAL AND VASCULAR AILMENTS

(75) Inventor: Richard A. Rosenbloom, Elkins Park, PA (US)

(73) Assignee: The Quigley Corporation, Doylestown, PA (US)

(*) Notice: Subject to any disclaimer, the term of this patent is extended or adjusted under 35 U.S.C. 154(b) by 271 days.

(21) Appl. No.: 10/288,825

(22) Filed: Nov. 6, 2002

(65) Prior Publication Data

US 2004/0087516 A1 May 6, 2004

(51) Int. Cl.
*A61K 35/78* (2006.01)

(52) U.S. Cl. ...................................................... 424/725
(58) Field of Classification Search .............. 424/195.1, 424/725; 514/783
See application file for complete search history.

(56) References Cited

U.S. PATENT DOCUMENTS

| | | | |
|---|---|---|---|
| 4,147,795 A | 4/1979 | Sarges | 424/273 |
| 4,210,667 A | 7/1980 | Sarges et al. | 424/224 |
| 4,232,040 A | 11/1980 | Waterbury | 424/283 |
| 4,250,097 A | 2/1981 | Pfister | 549/393 |
| 4,617,187 A | 10/1986 | Okuyama et al. | |
| 4,627,973 A * | 12/1986 | Moran et al. | 424/47 |
| 4,822,816 A | 4/1989 | Markham | |
| 5,011,840 A | 4/1991 | Sarges | 514/248 |
| 5,070,085 A | 12/1991 | Markham | |
| 5,550,249 A | 8/1996 | Della Valle et al. | 548/303.7 |
| 5,561,110 A | 10/1996 | Michaelis et al. | 514/13 |
| 5,571,441 A | 11/1996 | Andon et al. | |
| 5,595,982 A | 1/1997 | Harless | |
| 5,614,224 A | 3/1997 | Womack | |
| 5,648,083 A | 7/1997 | Blieszner et al. | |
| 5,665,360 A | 9/1997 | Mann | 424/195.1 |
| 5,686,082 A | 11/1997 | N'Guyen | |
| 5,709,868 A | 1/1998 | Perricone | |
| 5,770,260 A | 6/1998 | Fukuyama et al. | |
| 5,776,460 A | 7/1998 | Kim et al. | |
| 5,804,168 A | 9/1998 | Murad | |
| 5,824,666 A | 10/1998 | Deckner et al. | |
| 5,840,736 A | 11/1998 | Zelle et al. | 514/332 |
| 5,866,578 A | 2/1999 | Mylari et al. | 514/256 |
| 5,872,140 A | 2/1999 | Hesse et al. | |
| 5,876,737 A | 3/1999 | Schonrock et al. | |
| 5,883,086 A | 3/1999 | Craft | |
| 5,922,335 A | 7/1999 | Ptchelintasev | |
| 5,952,391 A | 9/1999 | Gers-Barlag et al. | |
| 5,958,379 A | 9/1999 | Regenold et al. | 424/47 |
| 5,972,359 A | 10/1999 | Sine et al. | |
| 5,972,999 A | 10/1999 | Murad | |
| 5,976,568 A | 11/1999 | Riley | |
| 5,976,579 A | 11/1999 | McLean | |
| 5,981,594 A | 11/1999 | Okamoto et al. | 514/573 |
| 5,998,394 A | 12/1999 | Voorhees et al. | |
| 6,048,886 A | 4/2000 | Neigut | |
| 6,051,602 A | 4/2000 | Bissett | |
| 6,054,128 A * | 4/2000 | Wakat | 424/765 |
| 6,069,168 A | 5/2000 | Horrobin et al. | 514/474 |
| 6,162,801 A | 12/2000 | Kita | |
| 6,296,861 B1 | 10/2001 | Perricone | |
| 6,299,896 B1 | 10/2001 | Cooper et al. | |
| 6,555,573 B1 | 4/2003 | Rosenbloom | |
| 6,592,896 B1 | 7/2003 | Rosenbloom | |
| 6,596,313 B1 | 7/2003 | Rosenbloom | |

FOREIGN PATENT DOCUMENTS

JP          07324037 A * 12/1995
WO       WO 97/18817        5/1997

OTHER PUBLICATIONS

Rona, Z.: Treating Periperal Neuropathy; Toronto Star, Aug. 2, 1998 pp. 1–2.*

Cunningham JJ, "The glucose/insulin system and vitamin C: implications in insulin–dependent diabetes mellitus", *J Am Coll Nutr* Apr. 1998;17(2):105–8 Abstract.

Crabbe MJ, et al., "Aldose reductase: a window to the treatment of diabetic complications?", *Prog Retin Eye Res* Jul. 1998;17(3):313–83 Abstract.

Fujita T, et al., "Inhibitory effects of perillosides A and C, and related monoterpene glucosides on aldose reductase and their structure–activity relationships", *Chem Pharm Bull* (Tokyo) Jun. 1995;43(6):920–6 Abstract.

Eaton RP, et al., "A commentary on 10 years of aldose reductase inhibition for limited joint mobility in diabetes", *J Diabetes Complications* Jan.–Feb. 1998;12(1):34–8 Abstract.

Costantino L, et al., "Diabetes complications and their potential prevention: aldose reductase inhibition and other approaches" *Med Res Rev*, Jan. 1999.;19(1):3–23 Abstract.

Benstead TJ, et al., "Nerve microvessel changes in diabetes are prevented by aldose reductase inhibition", *Can J Neurol Sci* Aug. 1995;22(3):192–7 Abstract.

(Continued)

*Primary Examiner*—Patricia Leith
(74) *Attorney, Agent, or Firm*—Knoble Yoshida & Dunleavy, LLC

(57) ABSTRACT

Compositions and methods for the treatment of peripheral neural and vascular ailments are disclosed. The method comprises administering a flavonoid compound with antioxidant properties, optionally formulated in a acceptable carrier. This compound or combination of compounds provides significant, effective relief of the symptoms of peripheral neural or vascular ailments. In addition, the compositions, when used according to the methods of the present invention, do not exhibit the severe side effects of many prior art compositions proposed for treatment of these ailments.

15 Claims, No Drawings

OTHER PUBLICATIONS

Okada Y, et al., "Search for naturally occuring substances to prevent the complications of diabetes. II. Inhibitory effect of coumarin and flavonoid derivatives on bovine lens aldose reductase and rabbit platelet aggregation" *Chem Pharm Bull (Tokyo)* Aug. 1995.;43(8):1385–7 Abstract.

Costantino L, et al., "1–Benzopyran–4–one antioxidants as aldose reductase inhibitors", *J Med Chem* Jun. 3, 1999;42(11):1881–93 Abstract.

Nishimura–Yabe C, "Aldose reductase in the polyol pathway: a potential target for the therapeutic intervention of diabetic complications" *Nippon Yakurigaku Zasshi* Mar.1998;111(3):137–45 Abstract.

Tomlinson DR, et al., "Aldose reductase inhibitors and their potential for the treatment of diabetic complications" *Trends Pharmacol Sci* Aug.1994;15(8):293–7 Abstract.

Airey M, et al., "Aldose reductase inhibitors for the prevention and treatment of diabetic peripheral neuropathy", *Cochrane Database Syst Rev* 2000;(2):CD002182 Abstract.

Maxwell SR, et al., "Antioxidant status in patients with uncomplicated insulin–dependent and non–insulin–dependent diabetes mellitus", *Eur J Clin Invest* Jun.1997;27(6):484–90 Abstract.

Himmerich S., et al., "Effect of Vitamins E and C on Nitric Oxide Production in Oxidized Low Density Lipoprotein Treated Human Aortic Endothelial Cells", *Academic Press*; 2000, internet download at http://www.academicpress.com/www/journal/niox/9204.html.

Asahi K, et al., "Nitric Oxide Inhibits the Formation of Advanced Glycation End Products", *Kidney Int* Oct.2000; 58(4):1780–7.

"Alternative Therapies for Diabetes" by National Diabetes Information Clearinghouse, May 1999.

Tiukavkima, et al., "Dihydorquercetin—a new antioxidant and biologically active food additive", Vopr Pitan 1997;(6):12–5 Abstract.

Plumb, et al., "Antioxidant properties of flavonal glycosides from tea", *Redox Rep* 1999;4(1–2):13–6 Abstract.

Duke, et al., "Biological Activities of CURCUMINOIDS", Phytochemical and Ethnobotanical Database.

Robak, et al., "Bioactivity of flavonoids", *Pol J Pharmacol* Nov.–Dec.1996;48(6):555–64 Abstract.

Bursel, et al., "Can protein kinase C inhibition and vitamin E prevent the development of diabetic vascularcomplications?", *Diabetes Res Clin Pract* Sep.1999; 45(2–3):169–82.

Freedman, et al., "Select flavonoids and whole juice from purple grapes ihibit platelet function and enhance nitric oxide release", *Circulation* Jun. 12, 2001; 103(23):2792–8 Abstract.

Lin, et al., "Recent studies on the biofunctions and biotransformations of curcumin", *Biofctors* 2000;13(1–4):153–8 Abstract.

Duarte, et al., "Vasodilator effects of quercetin in isolated rat vascular smooth muscle", *Eur J Pharmacol* Aug. 1993, 239:1–7 Abstract.

Giugliano, et al., "Oxidative stress and diabetic vascular complications", *Diabetes Care* Mar. 1996;19(3):257–67 Abstract.

Sports Medicine Articles (online), Sep. 1, 2000 (retrieved on Jan. 10, 2002) Retreived from the Internet http://www.rehabnet.com/Sports/Actinic%20Dermatitis.htm, p. 1–2.

Ohguro N, et al., "Topical Aldose reductase inhibitor for correcting corneal endothelial changes in diabetic patients", *Medscape Medline Abstract*, Dec. 1995.

Coles, L.S., M.D., "Quercetin:A Review of Clinical Applications", *Natural Medicine Online*, pp. 1–5.

Singh J.P., et al., "Role of Nitric Oxide in Pain", *Academic Press 2000*.

Kuroda, R., et al., "The Neuronal NO Synthase Inhibitor 7–nitro–indazole facilitates the antinociception elicited by the electrical stimulation of the secondary somatosensory cortex in the rat", *Academic Press*, 2000.

Mitchell, T., "Over–the Counter Drug is Treatment for Alzheimer's", *LE Magazine*, Nov. 2000, pp. 1–9.

Ross D, et al., "Ascorbate 6–palmitate–protects human erythrocytes from oxidative damage", *Free Radic Biol Med* Jan. 1999;26(1–2):81–9.

Medscape Medline Abstract, "Aldose reductase: a window to the treatment of diabetic complications?" by Crabbe MJ and Goode D. Jul. 1998.

Thirugnanasambantham P, et al., "Analgesic activity of certain flavone derivatives: a structure–activity study", *Clin Exp Pharmacol Physiol* Jan. 1993;20(1):59–63.

Guillausseau PJ, Preventive treatment of diabetic microangiopathy: blocking the pathogenic mechanisms Diabete Metab 1994;20(2 Pt 2):219–28.

McAuliffe AV, et al., Administration of ascorbic–acid and an aldose reductase inhibitor (tolrestat) in diabetes: effect on urinary albumin excretion., Nephron Nov. 1998;80(3):277–84.

Hosotani H., et al., "Effects of topical aldose reductase inhibitor CT–112 on corneal sensitivity of diabetic rats" Medscape Medline Abstract, Oct. 1996.

Haraguchi, Ho., et al., "Inhibition of aldose reductase by dihydroflavonols in Engelhardtia chrysolepis and effects on other enzymes", Medscape Medline Abstract, Jun. 1996.

Baton RP, et al. "A commentary on 10 years of aldose reductase inhibition for limited joint mobility in diabetes", Medscape Medline Abstract, Feb. 1998.

Medscape Medline Abstract, "Diabetes complications and their potential—prevention: aldose reductase inhibition and other approaches" by Costantino L, Rastelli G, Vianello P, Cignarella A, Barlocco D. Jan. 1999.

Rastelli C, et al., "Structural basics for the inhibition of aldose reductase by phenolic compounds", Medscape Medline Abstract, May 2000.

William F. Dial, *Cosmetic Dermatology*, "Topical Vitamin C May Help Protect Skin From UV Damage", Dec. 1991, pp. 34–35.

Bernard Idson, College of Pharmacy, University of Texas at Austin, Ultraviolet Irradiation Injury and Repair, Jan. 1992, pp. 22–24 and pp. 81–81.

Medscape Medline Abstract, "Nerve microvessel changes in diabetes are prevented by aldose reductase inhibition" by Benstead TJ, et al., Aug. 1995.

Darr et al., *British Journal of Dermatology*, "Topical vitamin C protects porcine skin from ultraviolet radiation–induced damage" (1992) 127, 247–253.

Medscape Medline Abstract, "Search for naturally occurring substances to prevent the complications of diabetes. II. Inhibitory effect of coumann and flavonoid derivatives on bovine lens aldose reductase and rabbit platelet aggregation" by Okada Y, et al., Aug. 1995.

Medscape Medline Abstract, "1–Benzopyran–4–one antioxidants as aldose reductase inhibitors" by Costantino L, et al., Jun. 1999.

Vitamin E (Tocopherol) vs. Vitamin E Acetate, Roche Vitamins for Cosmetics, pp. 1–5, Sep. 4, 1985.

Medscape Medline Abstract, "Aldose reductase in the polyol pathway: a potential target for the therapeutic intervention of diabetic complications" by Nishimura–Yabe C, Mar. 1998.

Medscape Medline Abstract, "Aldose reductase inhibitors and their potential for the treatment of diabetic complications" by Tomlinson DR, et al., Aug. 1994.

Medscape Medline Abstract, "Aldose reductase inhibitors for the prevention and treatment of diabetic peripheral neuropathy" by Airey M, et al., 2000.

Medscape Medline Abstract, "Antioxidant status in patients with uncomplicated insulin–dependent and non–insulin–dependent diabetes mellitus" by Maxwell SR, et al., Jun. 1997.

Himmerich S., et al., "F Effect of Vitamins E and C on Nitric Oxide Production in Oxidized Low Density Lipoprotein Treated Human Aortic Endothelial Cells" *Academic Press*, 2000.

Kohji, L., et al., "Nitric Oxide Inhibits the Formation of Advanced Glycation End Products" Academic Press, 2000.

McCarty ME, Medscape Medline Abstract, "Nitric oxide deficiency, leukocyte activation and resultant ischemia are crucial to the pathogenesis of diabetic retinopath/neuropathy—preventive potential of antioxidants, essential fatty acids, chromium, ginkgolides, and pentoxifylline" May 1998.

Boulton, AJ., et al., Medscape Medline Abstract, "Diabetic neuropathy" Jul. 1998.

Tutuncu NB., et al., Medscape Medline Abstract, "Reversal of defective nerve conduction with vitamin E supplementation in type 2 diabetes: a preliminary study" Nov. 1998.

Van Dam, PS, et al., Medscape Medline Abstract, "Diabetic peripheral neuropathy: international guidelines for prevention, diagnosis, and treatment (comment)" Feb. 2000.

Zangaro GA, et al., Medscape Medline Abstract. "Diabetic neuropathy: pathophysiology and prevention of foot ulcers" Mar. 1999.

Boulton, AJ., Medscape Medline Abstract, "Guidelines for diagnosis and outpatient management of diabetic peripheral neuropathy", *European Association for the Study of Diabetes*, Nov. 1998.

Feldman FL, et al., Medscape Medline Abstract, "Pathogenesis of diabetic neuropathy" 1997.

Medscape Medline Abstract, "Glyeoehelates and the etiology of diabetic *peripheral neuropathy*" by Qian NI and Eaton JW, Feb. 2000.

Galer, BS, et al., Medscape Medline Abstract, "Painful diabetic polyneuropathy: epidemiology, pain description, and quality of life" Feb. 2000.

Kaneto H.., et al., Medscape Medline Abstract, "Beneficial effects of antioxidants in diabetes: possible protection of pancreatic beta–cells against glucose toxicity", Dec. 1999.

Simon–Schnass, I.,et al., "Nutrient Intake of 130 Type II Diabetics".

DiSilvestro, R., "Zinc beticienev–Diabetes Link Explored" May 8, 2000, D.O~i8 "Alternative Therapies for Diabetes" by National Diabetes Infonnation Clearinghouse, May 1999.

Chusid, R., "Vitamins and Diabetes", 2000.

Salonen JT., et al., PubMed, "Increased risk of non–insulin dependent diabetes mellitus at low plasma vitamin F concentrations: a four year follow up study in men" Oct. 1995.

Fox GN, et al., PubMed, Chromium picolinate supplementation for diabetes mellitus, Jan. 1998.

Nutrition Dynamics Inc., "Glyco Control." 2000.

Diabetic Polyneuropathy, "Future Therapies", vol. 1, 1999, Medscape, Inc.

Diabetic Polyneuropathy, Pathophysiology, vol. 1 1999, Medscape, Inc.

Diabetic Polyneuropathy, Neurologic Examination vol., 1, 1999, Medscape, Inc.

Diabetic Polyneuropathy, "Symptom History", vol. 1, 1999, Medscape, Inc.

Van Acker, et al., "Structural Aspects of Antioxidant Activity of Flavonoids", pp. 245, 248, 249, 251, Oct. 2000.

Fukuoka N., et al., "Novel pharmacological activiey of a vitamin (novel pharmacological action of vitamin D)", Medscape Medline Abstract, Nippon Yakurigaku Zasshi Oct. 1997, 110 Suppl. 1:39P–43P.

Riaz, S., et al., "A vitamin D3 derivative (CB1093) induces nerve growth factor and prevents neurotrophic deficits in streptozotocin–diabetic rats", Medscape Medline Abstract, Diabetologia Nov. 1999, 42(11), 1308–1313.

Okada Y., et al., "Search for naturally occurring substances to prevent the complication of diabetes II. Inhibitory effect of coumarin and flavonoid derivatives on bovine lens aldose redusctase and rabbit platelet aggregation", Medscape Medline Abstract, Chem Pharm Bull (Yokyo) 1995, 43(8) 1385–1387.

Medscape Medline Abstract "Inhibitory effects of perillosides A and C, and related monoterpene glucosides on aldose reductase and their structure–activity relationships".

* cited by examiner

METHODS FOR THE TREATMENT OF PERIPHERAL NEURAL AND VASCULAR AILMENTS

BACKGROUND OF THE INVENTION

1. Field of the Invention

The present invention relates to compositions and methods for the treatment of peripheral neural and vascular ailments. In the methods of the present invention, a flavonoid is administered to a patient suffering from a peripheral neural or vascular ailment.

2. Brief Description of the Prior Art

The phrases "peripheral neuropathies" and "small fiber neuropathies" are used interchangeably herein to refer to a set of conditions characterized by functional changes or pathological changes, or both, in the small, unmyelinated nerve fibers of the peripheral nervous system.

Peripheral or small fiber neuropathies may be caused by any of about a hundred identified factors that can produce nerve damage. The cause may be metabolic, for example hypertriglyceridemia or pellagra. Toxic exposures may also cause small fiber neuropathies, for example those resulting from alcoholism, excessive doses of vitamin $B_6$, exposure to toxic metals such as thallium, or exposure to certain chemotherapeutic agents, such as vinca alkaloids. Certain congenital conditions, including amyloidosis, an-α-lipoproteinemia (Tangier's), and α-galactosidase (Fabry's), are known to cause small fiber neuropathies. Small fiber neuropathies may result from infections such as leprosy, or diseases such as AIDS, herpes simplex, herpes zoster (shingles), cytomegalovirus, hepatitis B and C, Lyme disease, autoimmune diseases, Fabry disease, diphtheria, vasculitis, and porphyria. In approximately 15% of cases, the cause of the small fiber neuropathy cannot be determined. The neuropathy is then referred to as idiopathic.

Patients afflicted with peripheral neuropathies have pain in their extremities. The pain may at first be perceived as a tingling sensation in the fingers or toes. Decreased sensitivity to heat or cold is also a common early symptom. Frequently, however, a physical examination will show that the patient's reflexes, strength, sensory levels, and electrophysiology are normal. This has historically complicated the diagnosis of peripheral neuropathies, or led to underdiagnosis, especially in the early stages of the neuropathies. Recent technology, however, including skin biopsies and measurement of the density of different nerve fiber types in the epidermis, has improved the likelihood of detecting peripheral neuropathies.

Small fiber or peripheral neuropathies tend to progress by spreading upward, and patients may develop intense pain and/or a burning sensation that can be so severe as to be debilitating. Other symptoms of these neuropathies include cold hands or feet, cramps, muscle weakness and/or atrophy, eventual loss of perception of pressure, pain and/or temperature, neuropathic ulcers, lack of sweating, dry eyes, dry mouth, impotence, and restless leg syndrome.

In some cases, treatment of the underlying cause may also reverse or alleviate small fiber neuropathies. When the underlying cause is unidentifiable or otherwise untreatable, however, treatment consists of reducing the symptoms of the neuropathies, typically by administering medications known to decrease pain from neuropathy and related conditions. These medications include tricyclic antidepressants, anticonvulsants, opioid medications, and local anesthetics applied to the painful area. An afflicted patient may also undergo physical and occupational therapy to improve mobility and function.

Often, the symptoms of peripheral neuropathies do not vary due to their underlying causes. For example, diabetic neuropathy, a type of peripheral neuropathy, is a fairly common long-term complication of diabetes mellitus that shares many of the symptoms of peripheral neuropathies and is, therefore, included among the peripheral neuropathies as defined herein. The cause of diabetic neuropathy, however, is believed to be a chronic systemic excess of the glucose metabolite sorbitol. Further, treating the underlying cause of diabetic neuropathy, that is, improving glycemic control, will often prevent the symptoms from worsening. Diabetic neuropathy is also known to be reversible, if good glycemic control is instituted while the condition is in its early stages.

Peripheral Neuropathies, including diabetic neuropathies, can also impair circulation in the affected area. Impaired circulation can adversely affect the appearance of the skin. Adverse effects on the appearance of the skin caused by radiation injury can include, for example, redness, discoloration, dryness of the skin.

"Peripheral vascular diseases" are diseases of the blood vessels outside the heart that lead to restriction or blockage of the blood vessels. Atherosclerosis, when it affects the extremities rather than the coronary arteries, is an example of a peripheral vascular disease. Peripheral vascular diseases may also be long-term complications of other diseases, such as Raynaud's disease, Raynaud's phenomenon, hypertension, or Buerger's disease (thromboangitis obliterans).

An early symptom of peripheral vascular disease includes pain upon exercising that is relieved by rest. These diseases are progressive, however, and patients may also experience numbness, muscle weakness or pain, loss of hair on the affected extremities, cyanosis, weak or absent pulse in the affected extremities, gait abnormalities, pain when resting, skin ulcers, and, eventually gangrene. Impaired circulation caused by peripheral vascular disease can also adversely affect the appearance of the skin. Adverse effects on the appearance of the skin caused by radiation injury can include, for example, redness, discoloration, dryness of the skin.

In general, an agent that promotes or induces angiogenesis, or one that at least partially clears blocked or restricted vessels, or one that will facilitate peripheral circulation by other means, i.e. by decreasing cellular adhesion, will be effective to treat peripheral vascular diseases.

Decreased microcirculation is also a long-term complication of diabetes. In general, a therapy that is effective for peripheral vascular diseases will also be effective to counter decreased microcirculation caused by diabetes.

There remains a need for a treatment for small fiber neuropathies that is clinically effective when the underlying cause of the neuropathy is unknown. A need also remains for an effective treatment for small fiber neuropathies that does not suffer from the disadvantage of causing severe side effects.

In addition, there remains a need for a clinically effective treatment of peripheral vascular ailments.

Accordingly, it is an object of certain embodiments of the present invention to provide a method that is effective for the treatment of small fiber neuropathies and peripheral vascular ailments.

It is another object of certain embodiments of the present invention to provide a method for the treatment of small fiber neuropathies or peripheral vascular ailments by administering a composition that does not cause severe side effects in the patient.

It is another object of certain embodiments of the present invention to provide a composition for the treatment of peripheral neuropathies or peripheral vascular ailments.

These and other objects of the present invention will be apparent from the summary and detailed descriptions of the invention that follow.

SUMMARY OF THE INVENTION

The present invention provides a method for the treatment of peripheral neural and vascular ailments by administering a composition including a therapeutically effective amount of a flavonoid having antioxidant properties, and, optionally, an acceptable carrier.

In another embodiment, the invention relates to a composition for treating peripheral neural and vascular ailments. The composition comprises a therapeutically effective amount of a mixture of a flavonoid having antioxidant properties, a therapeutically effective amount of a non-flavonoid antioxidant compound, and, optionally, an acceptable carrier.

DETAILED DESCRIPTION OF THE PREFERRED EMBODIMENTS

The compositions and methods of the invention provide significant, effective relief of symptoms of peripheral neural and vascular ailments, as well as partial recovery of lost microcirculation or neurological function in some cases. Surprisingly, the efficacy of the invention is not dependent on the underlying causes of the peripheral neural and vascular ailments. In addition, the composition used in the method of the invention, when administered in a therapeutically effective amount to treat peripheral neural and vascular ailments, does not cause severe side effects.

The topical compositions and methods of the invention also treat adverse effects on the appearance of the skin caused by peripheral neuropathies and/or peripheral vascular disease. These cosmetic benefits are obtained in patients having such disorders. Adverse effects on the appearance of the skin include, for example, redness, discoloration, dryness. Such cosmetic effects are intended to be included within the meaning of "treating ailments," although the effects relate to the appearance of skin in people using the composition and methods, Thus, the invention treats or cosmetically improves the appearance of persons having peripheral or neural vascular ailments by, for example, reducing or preventing redness of skin, reducing or preventing discoloration of skin, beautifying skin, improving appearance of skin, promoting attractiveness of skin, cleansing skin, removing dead or damaged skin or skin cells from skin and moisturizing skin.

The oral compositions and methods of the invention also provide nutritional and/or dietary benefits. These nutritional or dietary cosmetic benefits are obtained in patients having peripheral neuropathies and/or peripheral vascular disease. Such nutritional or dietary effects are also intended to be included within the meaning of "treating ailments." Thus, the invention offers dietary or nutritional benefits in supporting and/or maintaining neural, vascular and muscular health, maintains sensory integrity, i.e. sensations of hot and cold, and supports the maintenance of skin health.

The term "derivatives," as used herein, refers to structurally similar compounds that exhibit a common activity (e.g., antioxidant) and contain at least one significant, common structural element with the compound from which it is derived, which common structural element provides the common activity.

The expression "therapeutically effective amount," as used herein, refers to a nontoxic amount of a compound which is sufficient to provide the desired therapy to counteract small fiber neuropathies or peripheral vascular diseases. A therapeutic amount may, for example, reduce pain, reverse sensory fiber loss or demyelination, promote angiogenesis, increase microcirculation, or increase sensory perception. The exact amount required may vary, depending on the species, age, and general condition of the patient, the nature of the complications, the particular combination of compounds, the mode of administration, and the like. The term "therapeutically" is intended to encompass beneficial cosmetic effects and effects of improved nutrition as well as medical effects.

The compositions used in the method of the present invention include at least one flavonoid. Flavonoids are small organic compounds having a phenyl benzopyrone structure. They are found in the leaves, fruits, seeds, stems, or flowers of all vascular plants. Citrus fruits are a prominent source of flavonoids, over 4000 of which have been identified as deriving from plant sources. On average, the daily Western diet contains about one gram of mixed flavonoids.

Examples of flavonoids include, without limitation, flavonones, flavonols, anthocyanidins, proanthocyanidins, procyanidolic oligomers, biflavans, polyphenols, rutinosides, hydroxyethylrutinosides, and leucoanthocyanins.

Suitable flavonoids for use in the present invention include those that do not induce significant, adverse side effects when administered to a mammal in a therapeutically effective amount, and that do not react with any of the other ingredients of the composition used in the present invention to cause a substantial loss of activity of one or more compounds of the composition. Preferred flavonoids are obtained from natural sources. However, derivatives of such compounds may also be suitable for use in the present invention. Preferred flavonoids may be administered to humans without significant, adverse side effects when used in therapeutically effective amounts.

The selection of the flavonoid(s) included in the composition may be determined by factors such as toxicity, bioavailability, solubility or dispersability, and the like. Examples of flavonoids suitable for use in the present invention include, without limitation, (−)-epigallocatechin; (−)-epigallocatechin-gallate; 1,2,3,6-tetra-o-gallyol-β-d-glucose; 2'-o-acetylacetoside; 3,3',4-tri-o-methyl-ellagic acid; 6,3',4'-trihydroxy-5,7,8-trimethoxyflavone; 6-hydroxy-luteolin; 6-hydroxykaempferol-3,6-dimethyl ether; 7-o-acetyl-8-epi-loganic acid; acacetin; acetoside; acetyl trisulfate quercetin; amentoflavone; apigenin; apiin; astragalin; avicularin; axillarin; baicalein; brazilin; brevifolin carboxylic acid; caryophyllene; catechin; chrysin; chrysin-5,7-dihydroxyflavone; chrysoeriol; chrysosplenol; chrysosplenoside-a; chrysosplenoside-d; cosmosiin; δ-cadinene; curcumin; cyanidin; dihydroquercetin; dimethylmussaenoside; diacerylcirsimaritin; diosmin; diosmetin; dosmetin; ellagic acid; ebinin; epicatechin; ethyl brevifolin carboxylate; flavocannibiside; flavosativaside; galangin; gallic acid; genistein; ginkgo flavone glycosides; ginkgo heterosides; gossypetin; gossypetin-8-glucoside; haematoxylin; hesperidine; hispiduloside; hyperin; indole; iridine; isoliquiritigenin; isoliquiritin; isoquercitrin; jionoside;

juglanin; kaempferol; kaempferol-3-rhamnoside; kaempferol-3-neohesperidoside; kolaviron; licuraside; linariin; linarin; lonicerin; luteolin; luteolin-7-glucoside; luteolin-7-glucoronide; macrocarpal-a; macrocarpal-b; macrocarpal-d; macrocarpal-g; maniflavone; morin; methyl scutellarein; monoHER, diHER, triHER, tetraHER, myricetin; naringenin; naringin; nelumboside; nepetin; nepetrin; nerolidol; oligomeric proanthocyanidins; oxyayanin-a; pectolinarigenin; pectolinarin; pelargonidin; phloretin, phloridzin, polyphenols, including green tea polyphenols; quercetagetin; quercetin; quercimertrin; quercitrin; quercitryl-2" acetate; reynoutrin; rhamnetin; rhoifolin; rutin; scutellarein; sideritoflavone; silibin; silydianin; silychristine; silymarin; sophoricoside; sorbarin; spiraeoside; taxufolin; trifolin; vitexin; and wogonin, and the pharmaceutically acceptable salts; solvates; and derivatives of these compounds.

Preferred flavonoids are those that also have strong antioxidant properties. Examples of preferred flavonoids include, without limitation, (−)-epigallocatechin-3-gallate, catechin, rutin, quercetin, quercitrin, myricetin, kaempferol, myrecetrin luteolin, morin, fisetin, silymarin, apigenin, hesperitin, hesperidin, citrin, gossypetin, chrysin, oligomeric proanthocyanidins, biacalein, curcumin, gallic acid, epicatechin, dihydroquercetin, ginkgo flavone glycosides, ginkgo heterosides, silibin, silydianin silychristine, galangin, monoHER, diHER, triHER, tetraHER, naringenin, naringin, taxifolin, diosmin, phloretin, phloridzin, cyanidin, pelargonidin and derivatives thereof, and the pharmaceutically acceptable salts of these compounds.

More preferred flavonoids include, without limitation, quercetin, quercitrin, myricetin, rutin, kaempferol and myrecetrin. These compounds exhibit good antioxidant properties in combination with relatively low toxicity.

Advantageously, flavonoids and flavonoid derivatives may provide additional beneficial effects in the composition of the present invention. For example, quercetin acts as a chelator for transition metals. Flavonoids are also believed to possess anti-inflammatory activity and to assist in the stabilization of cell membranes, both activities that promote the treatment of small fiber neuropathies. Quercetin is also believed to have anticlastogenic properties. In addition, some flavonoids and flavonoid derivatives act as radical scavengers, reducing the concentration of hydroxyl radicals, for example, and thereby further enhancing the antioxidant effect of the composition used in the present invention.

Suitable non-flavonoid antioxidants for use in the present invention include those that exhibit antioxidant activity without causing any severe adverse side affects when administered in a therapeutically effective amount, and that do not react with any of the other ingredients of the composition used in the present invention to cause a substantial loss of activity of one or more compounds. Preferred antioxidants include those that occur naturally in the human body and materials obtained from plants or animals, or derivatives of such compounds.

Preferred non-flavonoid antioxidants include, without limitation, ascorbyl palmitate, ascorbic acid (vitamin C), vitamin A, vitamin E and its pharmaceutically acceptable esters (including but not limited to the acetate), α-lipoic acid, especially DL-α-lipoic acid, coenzyme Q10, glutathione (GSH), galangin, gingkolides, tocotrienols, carotenoids, cyanidin, curcuminoids, and derivatives thereof which exhibit antioxidant activity.

More preferably, mixtures of two or more antioxidants are employed in the composition used in the present invention. Derivatives of one or more of these compounds that exhibit antioxidant activity when administered in the compositions of the present invention may also be employed. The antioxidants may also be used in the form of their pharmaceutically acceptable salts. The salts may be preferred in some cases, for example to increase solubility or dispersability, or to reduce adverse side effects.

In a preferred embodiment, the antioxidant used in the composition of the present invention may comprise one or more antioxidant enzymes. The antioxidant enzymes useful in the present invention are those capable of scavenging radicals, of promoting radical scavengers or preventing radical formation. One or more of these antioxidant enzymes may act synergistically with one or more of the other antioxidants in the composition to scavenge free radicals more effectively and thereby aid in the prevention of cell damage in the skin. In a more preferred embodiment, the antioxidant enzyme used in the present invention is capable of absorption through the skin. Preferred antioxidant enzymes for use in the present invention include superoxide dismutase, catalase, glutathione peroxidase, methionine reductase, and the like.

In a more preferred embodiment, both quercetin and an antioxidant are included in the composition of the present invention. This combination of quercetin and an antioxidant results in an enhanced anti-oxidative effect. The antioxidant may be a flavonoid or a non-flavonoid.

Other compounds may also be included in the composition of the present invention to provide additional benefits, such as absorbability when applied topically, free radical scavenging, transition metal chelation, nitric oxide stabilization, analgesia, and anti-inflammatory activity. Some of these properties may have a beneficial effect on the pain of other related disorders such as fibromyalgia. Additional materials that may optionally be included in the compositions used in the present invention include inositol and other B-complex vitamins.

Some preferred compositions used in the invention also contain vitamin $D_3$, a vitamin $D_3$ analog, a compound that may be converted or metabolized into vitamin $D_3$ in the human body, or a metabolite of vitamin $D_3$.

Vitamin $D_3$, also known as cholecalciferol, may be further converted into another vitamin D intermediate, 25-hydroxycholecalciferol, in the liver by mitochondrial hydroxylase, in the presence of NADPH, and molecular oxygen.

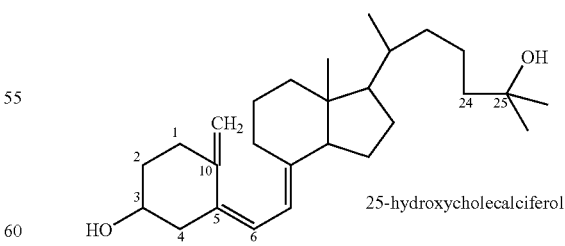

25-hydroxycholecalciferol

When a more active form of vitamin $D_3$ is required, 25-hydroxycholecalciferol is transported to the kidney where a new hydrolase enzyme is synthesized. This enzyme introduces another hydroxyl group at position 1, and the bioactive form of vitamin $D_3$, calcitriol, is produced.

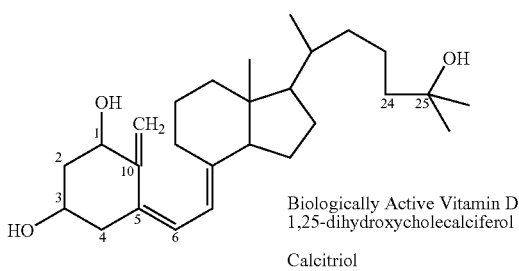

Biologically Active Vitamin D
1,25-dihydroxycholecalciferol
Calcitriol

An exemplary vitamin $D_3$ analog is 1(S), 3(R)-dihydroxy-20(R)-(1-ethoxy-5-ethyl-5-hydroxy-2-heptyn-1-yl)-9,10-seco-pregna-5(Z), 7(E), 10(19)-triene. An exemplary vitamin $D_3$ metabolite is 1, 25-dihydroxyvitamin $D_3$. Pharmaceutically acceptable salts of vitamin $D_3$ and its derivatives and metabolites may be employed in the methods of the present invention. Vitamin $D_3$ is particularly preferred for use in the present invention.

A dispersant may be necessary to facilitate the formulation of the vitamin $D_3$ or related compound. Suitable dispersants are well known to persons skilled in the art. Corn oil is one dispersant that is well suited for vitamin $D_3$ and related compounds. Also advantageously, corn oil is a natural product. The corn oil is used in an amount sufficient to disperse the vitamin $D_3$ or related compound.

The compositions used in the present invention may provide one or more of the following localized or systemic beneficial effects to a patient when administered in therapeutically effective amounts: relief of pain, burning, tingling, electrical sensations and/or hyperalgesia; increased microcirculation; nitric oxide stabilization; promotion of healing of skin ulcers and lesions; protein kinase C inhibition; decreased oxidative stress; anti-inflammatory activity; blockage of the formation of leukotrienes; stabilization of cell membranes; and promotion of the synthesis of nerve growth factor.

Compositions in accordance with the invention can provide additional effects of improving the appearance of the skin. Skin appearance may be adversely affected by peripheral neuropathies, including diabetic neuropathy, and/or peripheral vascular disease, or by other causes unrelated to the peripheral neuropathies and/or peripheral vascular disease being treated. One or more of the following beneficial properties may be realized when compositions of the invention are topically applied in an effective amount: reducing or preventing redness of skin, reducing or preventing discoloration of skin, beautifying skin, improving appearance of skin, promoting attractiveness of skin, cleansing skin, removing dead or damaged skin or skin cells from skin and moisturizing skin.

Without wishing to be held to a particular theory, there are several physiological processes that might be affected by an effective treatment for small fiber neuropathies. For example, an effective treatment might cause the degeneration of peripheral nerves to slow or to stop. Alternatively, an effective treatment might induce healing or regeneration of the damaged nerves. An effective treatment might also cause the generation of new nerves to replace the damaged nerves.

It is therefore expected that effective treatments for small fiber neuropathies will be applicable to other diseases or conditions affecting peripheral nerves. A method of regenerating nerves is beneficial to treat any patient suffering from nerve damage, for example, a skin graft patient or a victim of a nerve-severing trauma. In fact, many flavonoids are potent aldose reductase inhibitors. It has been shown that the oral administration of aldose reductase inhibitors increases the diameter of peripheral nerve bundles. Thus, it is expected that the methods of the present invention extend to the generation and regeneration of nerves.

Although the underlying cause of diabetic neuropathy is specifically known to be distinct from the other causes of small fiber neuropathies, the symptoms and pathologies are shared. It is therefore expected that an effective treatment for small fiber neuropathies will arrest, reverse, or alleviate certain symptoms of diabetic neuropathy.

Flavonoids promote microcirculation and therefore can also be used to treat peripheral vascular diseases. For example, the flavonoid quercetin supports vascular functioning in general, and therefore is an effective treatment for peripheral vascular diseases. Decreased microcirculation is believed to be caused at least in part by oxidative stress resulting from an excess of free radicals. Quercetin, an example of a flavonoid with antioxidant properties, is therefore an effective treatment for this condition. The chelating properties of flavonoids such as quercetin contribute to its effectiveness. The overabundance of sorbitol in the bloodstream of diabetic patients attracts metal ions, which are sequestered by chelation.

The compositions used in the present invention are preferably formulated with an acceptable carrier. The non-carrier ingredients may be combined with the carrier materials to produce a particular dosage form, or be customized for a particular treatment regimen. Thus, the amount of each ingredient may vary depending on such factors as the particular mode of administration, the activity of the particular compounds employed, the age, bodyweight, general health, sex, and diet of the patient, time of administration, rate of excretion, the combination of compounds, or the severity of the illness, among other potential factors.

A standard reference text on pharmaceutical formulations, Remington's Pharmaceutical Sciences, $18^{th}$ Ed., Mack Publishing Co. 1990, is incorporated herein by reference in its entirety.

It is well known in the art that the individual ingredients in formulated products may interact with each other. These interactions include, for example, chemical equilibria and other chemical or physical processes. These interactions may cause the original individual components of a formulated product to change over time. Such changes may be chemical or physical. For example, an acidic component may become deprotonated in a formulation that also contains a basic component. Alternatively, one or more components may precipitate or crystallize from a formulated product. Equilibria and other processes may be expected to increase in number and complexity with increasing numbers of components in a given formulation. Such equilibria and other processes may be either innocuous or deleterious to the activity of the formulated product.

The term "stable" as used herein refers to the property of retaining at least a portion of the intended activity over a certain period of time.

The terms "mixture," "composition" and "formulation" as used herein refer to stable mixtures, compositions, and formulations, respectively. Preferred mixtures, compositions, and formulations are stable over a period of at least about three months.

In the method of the present invention, the composition may be administered via several routes, including, without limitation, topically, orally, via an implanted reservoir, or by inhalation.

In a method of the invention, the composition is administered orally. An oral composition for use in the invention may be administered one to six times daily, or as needed to relieve pain and other symptoms of the small fiber neuropathies. Preferably, when administered orally, the composition is administered two to four times daily, as needed for pain. A sufficient amount should be administered to provide one or more of the beneficial effects of the compositions described above. The method initially treats acute symptoms but may be continued indefinitely to relieve pain, prevent symptoms from returning and possibly restore some nerve and/or skin function.

The oral compositions and methods of the invention also function as dietary or nutritional supplements. In this aspect of the invention, oral compositions and methods can maintain and/or support neural health, maintain and/or support vascular health and circulation, maintain and/or support muscular health, maintain sensory integrit, i.e. sensations of hot and cold, and support the health of the skin.

The oral compositions used in the present invention may be orally administered in any acceptable dosage form including, but not limited to, capsules, tablets, lozenges, troches, hard candies, powders, sprays, elixirs, syrups, and suspensions or solutions.

Suitable acceptable carriers for tablets include lactose and corn starch, for example. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin and gum acacia.

The composition used in the invention may be administered in capsule form, with or without diluents. Useful diluents for capsules include, without limitation, lactose and dried cornstarch. In addition, solid compositions similar to those of the tablets described above may be administered in soft and hard gelatin capsules.

The compositions used in the invention may be administered orally as encapsulated or unencapsulated suspensions, and they may comprise emulsifying and/or suspending agents such as are well known to those of skill in the art. Ancillary ingredients such as sweeteners, flavorants, coloring agents, dyes, and diluents such as water, ethanol, propylene glycol, glycerin and various combinations thereof may also be included in the oral formulations.

The compositions used in the present invention may also be administered by nasal aerosol or by inhalation. Appropriate formulations may be prepared using well-known techniques. For this method of administration, suitable carriers include, for example, saline and/or other conventional solubilizing or dispersing agents, optionally formulated with one or more preservatives, absorption promoters to enhance bioavailability, and/or fluorocarbons.

In a preferred method of the present invention, the composition is applied topically to an area of the skin in the vicinity of tissue that suffers from small fiber neuropathy in order to relieve pain and other symptoms of the small fiber neuropathy. Such areas typically include the patients' extremities, such as the fingers, toes, hands and feet, where neuropathy is often most pervasive.

Preferably, a suitable amount of the topical composition of the invention is applied one to six times daily, as needed. More preferably, the topical composition is applied two to four times daily, as needed. Also preferably, a sufficient amount of the topical composition is applied to cover the afflicted area with a thin layer of the composition and the composition is rubbed into the skin until little or no residue remains on the skin. The treatment is almost immediately effective to alleviate acute symptoms, and may be continued, for a predetermined period or indefinitely, to relieve pain, prevent the return of symptoms of small fiber neuropathies, and possibly restore some nerve and/or skin function.

A topical formulation of the composition used in the invention preferably includes an acceptable topical carrier. Many acceptable topical carriers are known to those of skill in the art. The compounds in the composition may be dissolved, dispersed and/or suspended in the topical carrier.

Suitable hydrophilic ointment bases are known to persons skilled in the art. Exemplary hydrophilic ointment bases suitable for use in the present invention are non-U.S.P. hydrophilic ointment bases such as those made by Fougera, Inc., a division of Altana, Inc. of Melville, N.Y. Sufficient hydrophilic ointment base is employed to act as a carrier for the compounds of the composition. Typically the hydrophilic ointment base will make up more than 80% of the total composition and more preferably 80–90% of the composition is the hydrophilic ointment base. The hydrophilic ointment base functions as a carrier and preferably enhances penetration of the compounds into the skin.

One preferred topical carrier comprises hydroxymethyl cellulose. Another preferred acceptable carrier includes a solution of an acrylic copolymer in a non-aqueous solvent system. The non-aqueous solvent system preferably contains a polyethylene glycol such as, for example, methoxy polyethylene glycol 550 (MPEG). One preferred MPEG is Sentry Carbowax MPEG 550 (Dow Corp., Midland, Mich.), which is suitable for use in foods, pharmaceuticals, and cosmetics. The acrylic copolymer is preferably present in a concentration range of 3–6% by weight of solution. Also preferably, the acrylic copolymer has a molecular weight of more than 20,000. More preferably, the acrylic copolymer has a molecular weight of more than 100,000, to substantially prevent absorption of the acrylic copolymer by the human body through the skin.

Preferably, the acceptable topical carrier independently provides benefits to the patient. For example, the topical carrier may comprise panthenol or a panthenol derivative. The panthenol derivatives useful in the present invention include at least D-panthenol, DL-panthenol, and mixtures thereof. Panthenol provides skin moisturizing properties, acts as a quick, deep penetrating component of the carrier, helps deliver the compounds through the skin to the area to be treated, and may impart a healing effect to damaged tissue. The amount of panthenol or panthenol derivative preferably ranges from 0.25 to 10 weight percent, more preferably from 0.5 to 5 weight percent, and, still more preferably, from 1 to 2 weight percent, based on the total weight of the topical composition.

The topical carrier of the present invention may employ other penetrants in addition to panthenol or as an alternative to panthenol. Exemplary penetrants include ethanol, oleic acid, sodium lauryl sulfate, isopropyl myristate, glycerol monooleate, caprylic/capric triglyceride, Crodamol GTC/C, glyceryl tricaprylate/caprate, Miglyol 810, Miglyol 812, MCT oil, Neobee M5, Nesatol, oleum neutrale, oleum vegetable tenue, thin vegetable oil, light mineral oil, stearyl alcohol and lanolin mixed with suitable vegetable oils or with soft paraffin. These penetrants may have an emollient effect and facilitate the absorption of ingredients of the topical composition of the present invention into the skin.

Preferably, the topical carrier of the present invention contains at least a hydrophilic ointment base, panthenol or a panthenol derivative, and one or more dispersants, if needed to disperse an insoluble or partially insoluble compounds in the carrier.

The topical carrier of the present invention may also include additional ingredients well known to persons skilled in the art, such as other carrier materials, other moisturizers, humectants, emollients, radiation blocking compounds, particularly UV-blockers, as well as other suitable materials that do not have a significant adverse effect on the activity of the topical composition in the amount used. A preferred additional ingredient for inclusion in the carrier is sodium acid phosphate, a moisturizer.

The topical composition of the present invention is preferably made by cold compounding, when one or more of the compounds employed in the topical composition are known to be sensitive to heat. Thus, in some cases, the stability or activity of the composition may be detrimentally affected as a result of other formulation methods. Preferably, a sufficient amount of the topical carrier is used, to provide a substantially homogeneous cream or ointment. It may be necessary to dissolve, disperse or suspend one or more of the ingredients prior to formulation in order to ensure substantially homogeneous distribution of one or more of the ingredients in the composition.

As noted above, dosages may vary with the manner of formulating the compounds. In general, the components of the composition, which include the flavonoid and the optional antioxidant, will make up from 0.5–90% by weight of the total composition to provide the desired daily dosage. The body weight dosages herein, when not normalized, are based on a patient having a body weight of 70 kg. The appropriate unit dosage may be determined by dividing the daily dosage by the number of unit doses per day.

The at least one flavonoid of the present invention is administered in a safe and effective amount. Every pound of a preferred topical composition of the present invention preferably includes about 1 to about 150 grams of one or more flavonoids, about 0.1 to about 50 grams of non-flavonoid antioxidants, and other suitable ingredients such as topical carriers.

Preferably, the flavonoid is used in an amount of about 2 to about 100 grams per pound of the composition. More preferably, the flavonoid is employed in an amount of about to about 10–50 grams per pound of the composition, and, still more preferably, about 15 to about 40 grams per pound of the composition.

When vitamin $D_3$ or a derivative or metabolite thereof is used in the composition, the ratio of the amount of that compound to the amount of the flavonoid employed in the compositions of the present invention is from about 200 IU per gram of antioxidant to about 3 million IU per gram of flavonoid. More preferably, the composition contains about 1800 IU to about 1 million IU of nerve growth factor synthesis promoter per gram of flavonoid, and, still more preferably, about 5000 IU to about 200,000 IU of nerve growth factor synthesis promoter per gram of flavonoid.

When the composition includes both vitamins A and $D_3$, they are preferably formulated together in a corn oil dispersion. Generally, each cubic centimeter (cc) or milliliter (mL) of the corn oil dispersion contains about 500,000 to about 2,000,000 IU of vitamin A and about 50,000 to about 200,000 IU of vitamin $D_3$. Preferably, every milliliter of the corn oil contains about 800,000 to about 1,200,000 IU of vitamin A and about 80,000 IU to about 120,000 IU of vitamin $D_3$. More preferably, the composition used in the invention contains about 1,000,000 IU and about 100,000 IU of vitamins A and $D_3$, respectively.

When a composition including vitamin $D_3$ or derivative or metabolite of vitamin $D_3$ is administered, the vitamin $D_3$ or derivative or metabolite of vitamin $D_3$ is used in a safe and effective amount. More preferably, an amount of about 6 to about 14.3 IU per kg of body weight of the patient for each administration. More preferably, an amount of about 8 to about 14.3 IU per kg body weight of the patient, and, still more preferably, an amount of about 10 to about 13 IU is employed per kg of body weight of the patient, is administered.

The flavonoid is preferably used in an amount that provides substantially the same level of activity as a daily dose of about 13 to about 22 mg/kg bodyweight of quercetin. More preferably, the flavonoid is administered in an amount that provides substantially the same level of activity as a daily dose of about 17.2 to about 21.4 mg/kg bodyweight of quercetin, and, still more preferably, an amount that provides substantially the same level of activity as a daily dose of about 18 to about 21 mg/kg bodyweight of quercetin.

About 11 to about 29 mg/kg bodyweight/day of ascorbyl palmitate may be administered. More preferably, about 14.3 to about 28.6 mg/kg bodyweight/day is administered.

When vitamin E is administered in the form of mixed tocopherols, the daily dosage is preferably about 4 to about 12 IU per kg bodyweight. More preferably, the daily dosage is about 5.7 to about 11.4 IU per kg bodyweight. Still more preferably, the daily dosage of mixed tocopherols is about 6 to about 10 IU per kg bodyweight. When vitamin E is administered in another form, an amount is administered that provides an equivalent effect as the above-described amounts of mixed tocopherols.

When vitamin A is administered, the daily dosage is preferably about 170 to about 360 IU per kg bodyweight per day. More preferably, the dosage is about 214.3 to about 357.1 IU per kg bodyweight per day. Still more preferably, the dosage is about 220 to about 340 IU per kg bodyweight per day.

Every pound of a preferred topical composition of the present invention preferably includes about 2 to about 50 grams of one or more flavonoids, about 1 to about 50 grams of non-flavonoid antioxidants, as well as other suitable ingredients such as topical carriers.

The witch hazel extract may be used in an amount of about 2.5–40 cc, more preferably of about 5–30 cc, and most preferably of about 10–20 cc per pound of topical base. The glycerine humectant may be used in an amount of about 2–20 cc, more preferably of about 3.5–15 cc, and most preferably of about 5–10 cc per pound of topical base. The apricot kernel oil may be used in an amount of about 0.5–5 cc, more preferably of about 0.5–4 cc, and most preferably of about 1–3 cc per pound of topical base. The AJIDEW NL-50 NaPCA (50% aqueous solution) may be used in an amount of about 15–45 cc, more preferably of about 20–40 cc, and most preferably of about 25–35 cc per pound of topical base.

A more preferred topical composition of the invention can be made using the following ingredients: about 25 to about 35 cc of a 50% aqueous solution of AJIDEW NL-50 NaPCA (50% aqueous solution) moisturizing agent, about 5 to about 10 cc of D- or DL-panthenol, and about 10 to about 50 grams of quercetin powder.

The above amounts are appropriate for combination with one pound of hydrophilic ointment base. As is well known in the art, larger amounts of one or more components, e.g. an antioxidant, can be employed while reducing the amount of another component of the same type or having a similar type of activity.

In a preferred embodiment, about 10 g/kg bodyweight of quercetin is used. In another preferred embodiment, about 5 g/kg bodyweight to about 25 g/kg bodyweight, more preferably about 5 g/kg bodyweight, of rutin are added to the composition. In another preferred embodiment, about 10 g to about 50 g/kg bodyweight, more preferably about 10 g/kg bodyweight, of glutathione are added to the composition.

In one embodiment of the present invention, the compositions are substantially free of cinnamic acid derivatives of the formula:

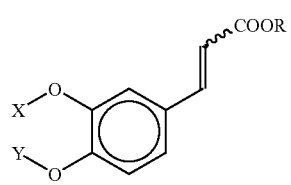

wherein the groups X, Y and R, independently of one another, can be chosen from the group consisting of H and branched or unbranched alkyl having 1–18 carbon atoms, acids thereof, and physiologically tolerated salts thereof.

The following examples are provided to describe the invention in further detail. These examples, which set forth a preferred mode presently contemplated for carrying out the invention, are intended to illustrate and not to limit the invention.

EXAMPLE 1

A topical composition including a mixture of an hydrophilic ointment base, sodium acid phosphate moisturizing agent, and DL-panthenol, formulated together as the acceptable carrier, and further including quercetin was prepared by cold compounding. The formulation of the composition is given in Table 1. The formulation may optionally be supplemented with coenzyme Q10 (500 mg) and may optionally contain another antioxidant.

The composition was prepared by first placing the hydrophilic ointment base in a stainless steel bowl and mixing briskly until the ointment became creamy. The sodium acid phosphate, panthenol, quercetin, and other anti-oxidant, if any, were next added in that order. After each ingredient was added, mixing was continued until no traces of dry ingredients were visible and a substantially homogeneous mixture was obtained. The final color was a consistent yellow and the cream had the consistency of cake frosting. The mixture was stored in a sterile container. All containers and tools that contact the composition during mixing must also be sterilized with, for example, zephiran chloride, a bleach solution, or betadine.

This composition can be topically administered, under the supervision of a physician, to patients diagnosed with small fiber neuropathies. The topical composition may be applied, for example, twice daily in the morning and afternoon, or up to six times daily, as needed for pain relief, over a period of a few days. Treated patients are predicted to experience positive results that will last up to a day or two after treatment is discontinued.

TABLE 1

| Ingredient | Amount |
| --- | --- |
| Hydrophilic ointment base | 1 lb |
| 50% aqueous solution of Sodium acid phosphate | 25 cc |
| DL-panthenol | 5 cc |
| Quercetin powder | 10 g–50 g |
| Other Antioxidant | 10 g–50 g |

Other combinations of compounds suitable for use in the methods of the invention are set forth in Examples 2 through 7. The compounds may be combined with about 1 lb of hydrophilic ointment base for topical administration.

EXAMPLE 2

A topical composition was formulated using the ingredients listed in Table 2 below.

TABLE 2

| Ingredient | Amount |
| --- | --- |
| White Petrolatum | 5,760.0 g |
| Stearyl Alcohol | 4,030.0 g |
| Isopropyl Palmitate | 1,730.0 g |
| Apricot Kernal Oil | 140.5 g |
| Vitamin A Palmitate and Vitamin $D_3$ in corn oil dispersion | 140.5 g |
| DL-α-tocopheryl acetate | 47.7 g |
| Butylated Hydroxy Anisole | 13.25 g |
| Methylparaben | 5.83 g |
| Propylparaben | 3.45 g |
| Sodium Lauryl Sulfate | 230.6 g |
| Propylene Glycol | 2,766.6 g |
| DL-Panthenol, 50% in water | 304.8 g |
| Sodium L-Pyrrolidone Carboxylic Acid (50% in water) | 1,598.0 g |
| Purified Water | 8,500.0 g |
| Glycerin | 318.0 g |
| Ascorbyl Palmitate | 100.7 g |
| Quercetin Dihydrate | 204.1 g |
| Witch Hazel Extract | 598.9 g |

The composition of Table 2 was topically administered three times per day over a period of 4 weeks to 24 patients suffering from diabetic neuropathy in at least one foot as a result of having Type 1 or Type 2 diabetes mellitus in a placebo-controlled, double blind proof of concept study conducted in France. 12 patients received a placebo consisting of the composition of Table 2 except that the ascorbyl palmitate and quercetin dihydrate were left out. Eligible patients were screened using the Michigan Neuropathy Screening Instrument (MNSI), Feldman, E. L., et al., "A Practical Two-Step Quantitative Clinical and Electrophysiological Assessment for the Diagnosis and Staging of Diabetic Neuropathy," *Diabetes Care,* 1994, pp. 1281–1289.

5.3 ml of the topical ointment was topically administered to the affected area three times per day. Treatment was assessed using both a detailed symptom assessment and a quality of life questionnaire.

The results of the test were positive. The formulation produced a significant decrease of diabetic peripheral neuropathy pain and discomfort, and an improvement in the appearance and texture of the skin, including reduced dryness. A similar formulation without ascorbyl palmitate was also effective on diabetic skin and aging skin, as well as providing relief from the discomfort of diabetic peripheral neuropathy and small fiber peripheral neuropathy.

EXAMPLE 3

| Ingredient | Amount |
| --- | --- |
| Hydrophilic ointment base | 1 lb |
| 50% aqueous solution of Sodium acid phosphate | 25 cc |
| DL-panthenol | 5 cc |

-continued

| Ingredient | Amount |
| --- | --- |
| Quercetin powder | 10 g–50 g |
| Glutathione | 10 g–50 g |

EXAMPLE 4

| Ingredient | Amount |
| --- | --- |
| Hydrophilic ointment base | 1 lb |
| 50% aqueous solution of Sodium acid phosphate | 25 cc |
| DL-panthenol | 5 cc |
| Quercetin powder | 10 g–50 g |
| Rutin | 5 g–25 g |

EXAMPLE 5

| Ingredient | Amount |
| --- | --- |
| Ascorbyl Palmitate | 2 g |
| Hesperidine | 2 g |
| Rutin | 20 g |
| Vitamins A and $D_3$ | 3 cc |
| Vitamin E acetate | 1 cc |
| DL Panthenol 50-L | 5 cc |

EXAMPLE 6

| Ingredient | Amount |
| --- | --- |
| Ascorbyl Palmitate | 2 g |
| Ascorbyl glucosamine | 1 g |
| Luteolin | 15 g |
| Vitamins A and $D_3$ | 3 cc |
| Vitamin E acetate | 1 cc |
| DL-Panthenol 50-L | 5 cc |

EXAMPLE 7

| Ingredient | Amount |
| --- | --- |
| Ascorbyl glucosamine | 2 g |
| Apigenin | 15 g |
| Vitamins A and $D_3$ | 3 cc |
| Vitamin E acetate | 1 cc |
| DL Panthenol 50-L | 5 cc |

EXAMPLE 8

| Ingredient | Amount |
| --- | --- |
| Ascorbyl palmitate | 2 g |
| Gamma linolenic acid | 10 g |
| Rutin | 15 g |

-continued

| Ingredient | Amount |
| --- | --- |
| Vitamins A and $D_3$ | 3 cc |
| Vitamin E acetate | 1 cc |
| DL Panthenol 50-L | 5 cc |

Although the present invention has been described and exemplified in terms of certain preferred embodiments, other embodiments will be apparent to those skilled in the art. The invention is, therefore, not limited to the particular embodiments described and exemplified, but is capable of modification or variation. The full scope of the invention is delineated by the appended claims.

What is claimed is:

1. A method of treating diabetic neuropathy comprising the step of topically administering to a patient having a diabetic neuropathy a composition comprising a therapeutically effective amount of quercetin and an effective amount of one or more compounds selected from the group consisting of: vitamin $D_3$, 1(S),3-(R)-dihydroxy-20-(R)-1-ethoxy-5-ethyl-5-hydroxy-2-heptyn-1-yl)-9,10-seco-pregna-5(Z), 7(E), 10 (19)-triene, compounds that may be converted or metabolized into vitamin $D_3$ in the human body, metabolites thereof, and pharmaceutically acceptable salts thereof.

2. The method as claimed in claim 1, wherein the composition further comprises an acceptable carrier comprising a sufficient amount of a panthenol selected from D-panthenol and DL-panthenol to promote penetration of one or more compounds of the composition into the skin.

3. The method as claimed in claim 2, wherein the acceptable carrier comprises a sufficient amount of at least one non-U.S.P. hydrophilic ointment base to form a topical composition.

4. The method of claim 3, wherein the composition comprises, DL-panthenol, quercetin, vitamin $D_3$, and an antioxidant.

5. The method of claim 3, wherein the composition comprises a hydrophilic ointment base, 1 to 10 cc of DL-panthenol per pound of the composition, 10 g to 50 g of quercetin per pound of the composition, 200 IU to 3 million IU of vitamin $D_3$ per gram of said quercetin, and 1–50 grams of vitamin E acetate per pound of the composition.

6. The method of claim 1, wherein the compound comprises vitamin $D_3$.

7. The method of claim 6, wherein the composition further comprises vitamin E acetate.

8. The method of claim 7, wherein the composition comprises 10–50 grams of quercetin per pound of the composition, 1800 IU to 1 million IU of vitamin $D_3$, per gram of quercetin, and 1–50 grams of vitamin E acetate, per pound of the composition.

9. The method of claim 1, wherein the composition further comprises at least one non-flavonoid antioxidant selected from the group consisting of ascorbyl palmitate, ascorbic acid, vitamin A, vitamin E and its pharmaceutically acceptable esters, α-lipoic acid, coenzyme Q10, glutathione, a polyphenol, a component of green tea, and pharmaceutically acceptable salts thereof.

10. The method of claim 9, wherein the non-flavonoid antioxidant comprises glutathione.

11. The method of claim 9, wherein the non-flavonoid antioxidant comprises a component of green tea.

12. The method of claim 9, wherein the non-flavonoid antioxidant comprises vitamin E acetate.

13. The method of claim 1, wherein treating peripheral neural ailments comprises treating a systemic effect of the peripheral neural ailment.

14. The method of claim 1, wherein treating peripheral neural ailments comprises treating a local effect of the peripheral neural ailment.

15. The method of claim 1, wherein treating a peripheral neural ailment is selected from the group consisting of decreasing pain, decreasing tingling, normalizing sensitivity to heat or cold, decreasing cramping, decreasing muscle weakness, decreasing numbness, and improving peripheral circulation.

* * * * *